(12) United States Patent
Taylor-Kennedy

(10) Patent No.: US 7,000,615 B2
(45) Date of Patent: Feb. 21, 2006

(54) ANTI-AIRWAY OBSTRUCTION STRAP

(76) Inventor: Lisa Carole Taylor-Kennedy, 116 Lakeview Dr., Sunnyvale, TX (US) 75182

( * ) Notice: Subject to any disclaimer, the term of this patent is extended or adjusted under 35 U.S.C. 154(b) by 0 days.

(21) Appl. No.: 10/757,094

(22) Filed: Jan. 14, 2004

(65) Prior Publication Data

US 2004/0144390 A1   Jul. 29, 2004

Related U.S. Application Data

(60) Provisional application No. 60/440,086, filed on Jan. 16, 2003.

(51) Int. Cl.
*A61F 11/00* (2006.01)
(52) U.S. Cl. .................................................. 128/857
(58) Field of Classification Search .................... 2/171, 2/171.2; 128/857, 848, 846
See application file for complete search history.

(56) References Cited

U.S. PATENT DOCUMENTS

| | | | | |
|---|---|---|---|---|
| 3,776,244 A | * | 12/1973 | Morgan | 132/273 |
| 4,207,881 A | * | 6/1980 | Richter | 602/17 |
| 4,650,182 A | * | 3/1987 | Ross | 482/11 |
| 4,934,357 A | * | 6/1990 | Frantzich et al. | 602/61 |
| 5,787,894 A | * | 8/1998 | Holt | 128/848 |
| 5,893,365 A | * | 4/1999 | Anderson | 128/848 |
| 6,248,043 B1 | * | 6/2001 | Morton | 482/11 |
| 6,277,053 B1 | * | 8/2001 | Desembrana | 482/11 |

* cited by examiner

*Primary Examiner*—Henry Bennett
*Assistant Examiner*—Camtu Nguyen
(74) *Attorney, Agent, or Firm*—W. Thomas Timmons

(57) ABSTRACT

A strap is disclosed for a human user. The strap includes a support for the chin of the user, a first support for a first mandible of the user, a second support for the second mandible of the user, and means for securing the strap to the head of the user. The first mandible support is affixed to one side of the chin support and the second mandible support is affixed to the opposite side of the chin support. In a preferred form, the first mandible support and the second mandible support are each from about 1.5 inches wide to about 3 inches wide, and in a preferred range, the first mandible support and the second mandible support are each from about 1.75 inches wide to about 2.25 inches wide. In a preferred embodiment of a strap according to the present invention, the first mandible support is at an angle to the second mandible support of from about 90 degrees to about 140 degrees when the strap is opened flat, as it would be before it is place on the user. In a preferred range, when the strap is opened flat, the first mandible support is at an angle to the second mandible support of from about 100 degrees to about 120 degrees. Typically, when the strap is opened flat, the first mandible support is at an angle to the second mandible support of approximately 110 degrees. In a preferred form, the chin support is at an angle to the main plane of the strap of from about 40 degrees to about 80 degrees when the strap is closed. A preferred range for the chin support is at an angle to the main plane of the strap of from about 50 degrees to about 70 degrees. Typically, the chin support is at an angle to the main plane of the strap of approximately 60 degrees.

18 Claims, 2 Drawing Sheets

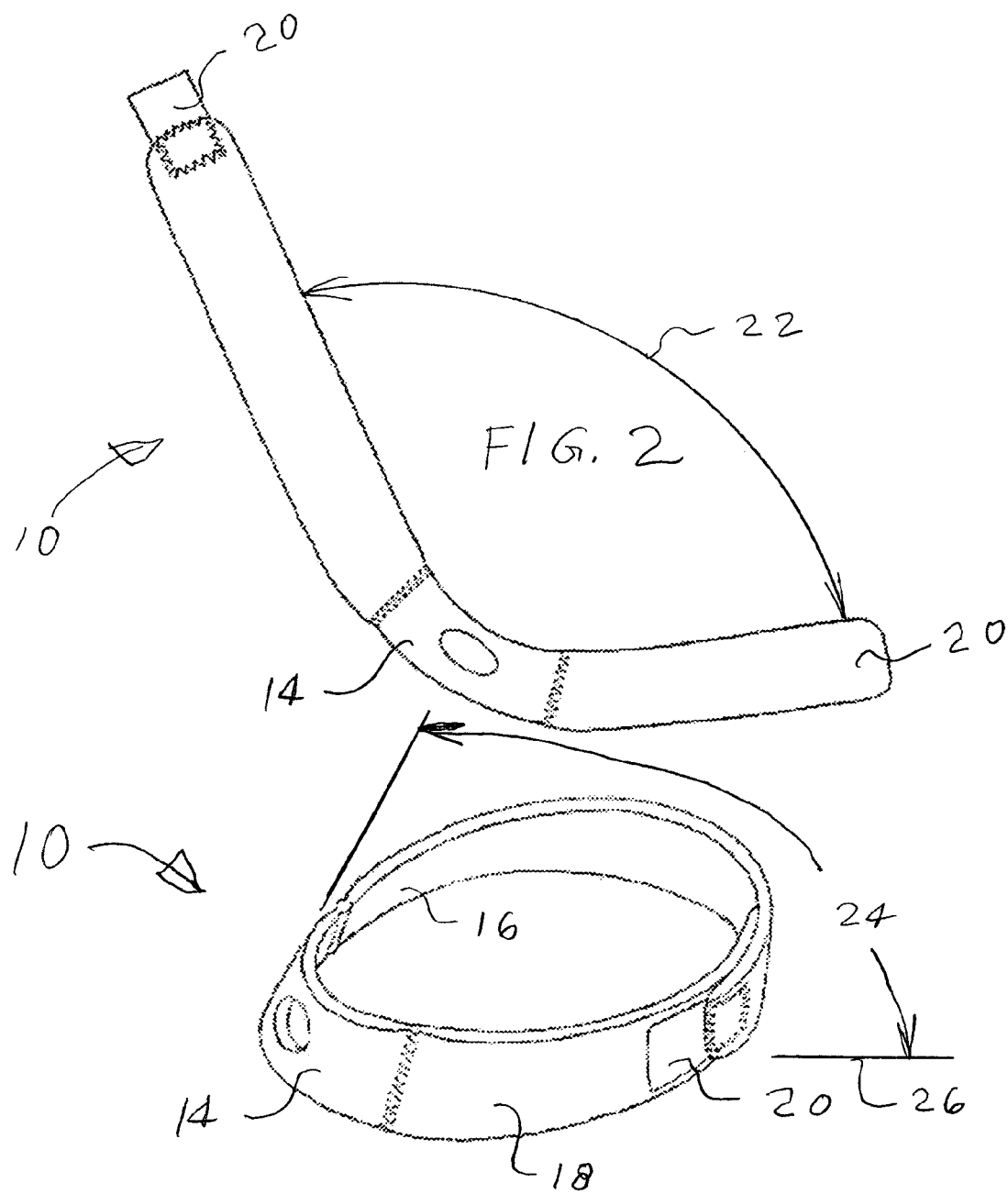

ANTI-AIRWAY OBSTRUCTION STRAP

This application claims the benefit of provisional application No. 60/440,086 filed Jan. 16, 2003.

BACKGROUND OF THE INVENTION

1. Field of the Invention

The present invention relates generally to devices for the prevention of airway obstruction, and in one of its aspects to a medical device for use by an anesthesiologist during surgery.

2. Description of Related Art

In the scope of medicine and under drug induced sleep or sedation, the standard of care according to the American Society of Anesthesiologists for monitoring includes that which assist in determining depth of anesthesia. Additionally, monitoring end tidal $CO_2$, increases the margin of safety for patients under anesthesia.

Often under anesthesia, patients have decreased muscle tone and their mandibles become relaxed. Subsequently, patients may become mouth-breathers or experience airway obstruction and end tidal $CO_2$ cannot be monitored.

Chin straps are well known. Various chin straps are shown in U.S. Pat. No. 5,787,894, No. 6,119,694 and No. 6,279,577. Such chin straps do not give support for the mandibles, and are, therefore, not well suited for certain medical procedures. When used with CPAP and BIPAP machines for breathing, they can lead to "mouth leaks."

SUMMARY OF THE INVENTION

A strap according to the present invention is for a human user, although it may be put into place by an anesthesiologist or other doctor. The strap includes a support for the chin of the user, a first support for a first mandible of the user, a second support for the second mandible of the user, and means for securing the strap to the head of the user. Such a means can be a Velcro strap, snaps, an elastic strap, a buckle or any other means. The first mandible support is affixed to one side of the chin support and the second mandible support is affixed to the opposite side of the chin support.

In a preferred form, the first mandible support and the second mandible support are each from about 1.5 inches wide to about 3 inches wide, and in a preferred range, the first mandible support and the second mandible support are each from about 1.75 inches wide to about 2.25 inches wide.

In a preferred embodiment of a strap according to the present invention, the first mandible support is at an angle to the second mandible support of from about 90 degrees to about 140 degrees when the strap is opened flat, as it would be before it is place on the user. In a preferred range, when the strap is opened flat, the first mandible support is at an angle to the second mandible support of from about 100 degrees to about 120 degrees. Typically, when the strap is opened flat, the first mandible support is at an angle to the second mandible support of approximately 110 degrees.

In a preferred embodiment of a strap according to the present invention, the chin support is at an angle to the main plane of the strap of from about 40 degrees to about 80 degrees when the strap is closed. A preferred range for the chin support is at an angle to the main plane of the strap of from about 50 degrees to about 70 degrees. Typically, the chin support is at an angle to the main plane of the strap of approximately 60 degrees.

These and other objects, advantages and features of this invention will be apparent from the following description taken with reference to the accompanying drawing, wherein is shown a preferred embodiment of the invention.

BRIEF DESCRIPTION OF THE DRAWING

FIG. 2 is a plan view of the strap of FIG. 1 in an open position; and

FIG. 3 is a top left perspective view of the strap of FIG. 1 in a closed position.

DESCRIPTION OF THE PREFERRED EMBODIMENT

Figure 1:
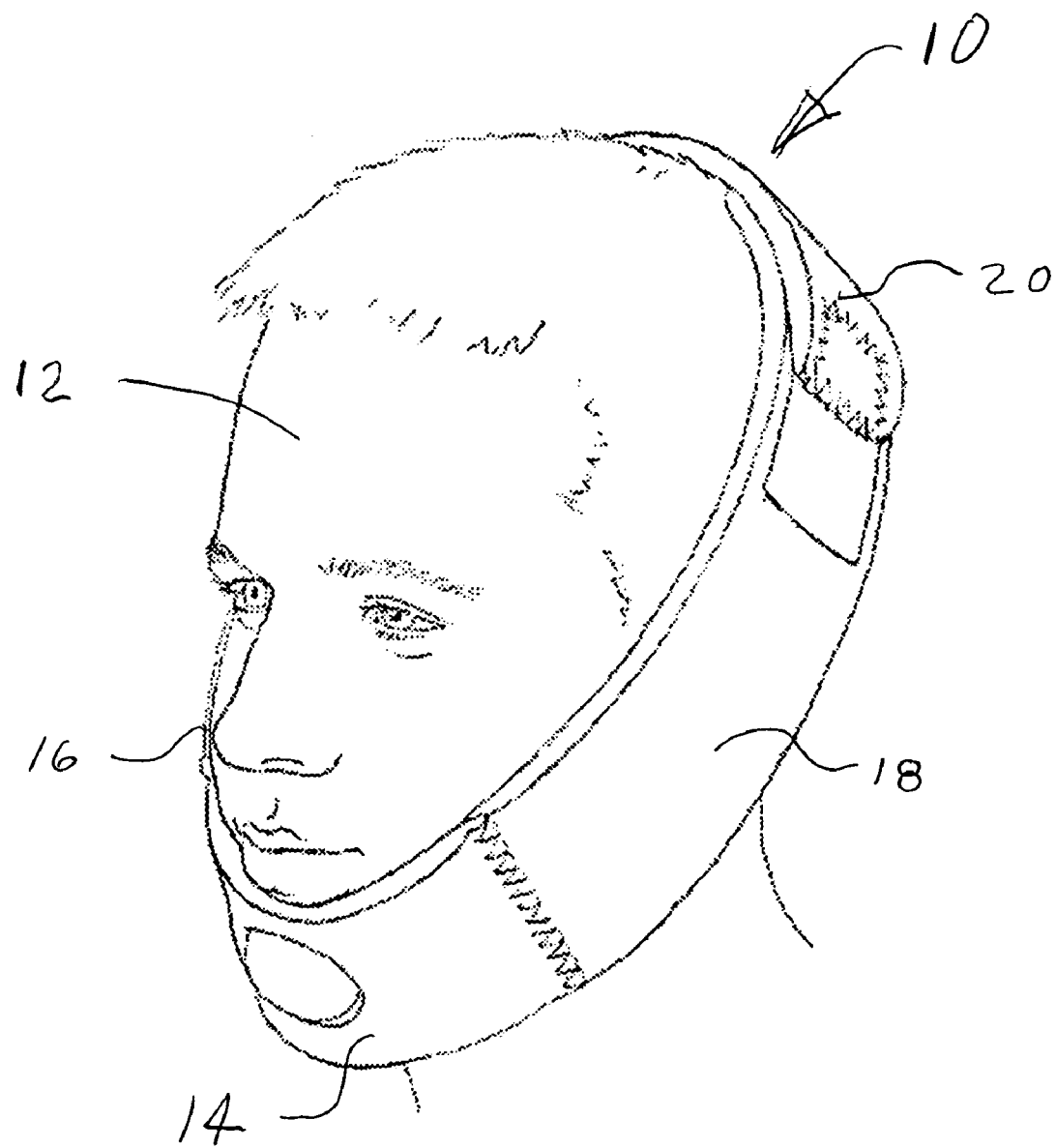
FIG. 1 is a left front perspective view of a strap according to the present invention in place on a user.

Referring now to the drawing, and in particular to FIG. 1, a strap according to the present invention is referred to generally by reference numeral 10. The strap is for a human user 12, although it may be put into place by an anesthesiologist or other doctor. The strap includes a support 14 for the chin of the user, a first support 16 for a first mandible of the user, a second support 18 for the second mandible of the user, and means 20 for securing the strap to the head of the user. Such a means can be a Velcro strap, snaps, an elastic strap, a buckle or any other means. First mandible support 16 is affixed to one side of chin support 14 and second mandible support 18 is affixed to the opposite side of the chin support.

In a preferred form, first mandible support 16 and second mandible support 18 are each from about 1.5 inches wide to about 3 inches wide, and in a preferred range, the first mandible support and the second mandible support are each from about 1.75 inches wide to about 2.25 inches wide.

In a preferred embodiment of a strap according to the present invention, the first mandible support is at an angle 22 to the second mandible support of from about 90 degrees to about 140 degrees when the strap is opened flat, as it would be before it is place on the user. In a preferred range, when the strap is opened flat, the first mandible support is at an angle to the second mandible support of from about 100 degrees to about 120 degrees. Typically, when the strap is opened flat, the first mandible support is at an angle to the second mandible support of approximately 110 degrees. In a preferred form, it is made from an air permeable nylon blend fabric that is about 2 inches wide and about 24 inches long with a 3 inch long Velcro brand closure.

In a preferred embodiment of a strap according to the present invention, the chin support is at an angle 24 to the main plane 26 of the strap of from about 40 degrees to about 80 degrees when the strap is closed. A preferred range for the chin support is at an angle to the main plane of the strap of from about 50 degrees to about 70 degrees. Typically, the chin support is at an angle to the main plane of the strap of approximately 60 degrees.

Indications and usage are to maintain mouth closure, elevation of chin/mandible to prevent or relieve airway obstruction. Hospital use includes operating rooms when sedation is used, while utilizing supplemental oxygen via nasal prongs and carbon dioxide sampling through nasal prongs.

Often under anesthesia, patients have decreased muscle tone and their mandibles become relaxed. Subsequently, patients may become mouth-breathers or experience airway obstruction and end tidal $CO_2$ cannot be monitored. An anti-airway obstruction strap according to the present invention can alleviate the aforementioned problem and improve the safety of the anesthetic. In particular, a strap according to the present invention supports the mandibles and not just the chin, thus giving support which more closely approximates the manual support given by an anesthesiologist.

When inducing general anesthesia, prior to intubation or placement of an endotracheal tube, the anti-airway obstruction strap of the present invention will help maintain a patent airway and aid in preoxygenation. The anti-airway obstruction strap can be utilized in high-risk patient population, such as obesity.

Additionally, snoring, mouth breathing, obstructive sleep apnea and other airway obstruction may be alleviated with this anti-airway obstruction strap in non-hospital use.

From the foregoing it will be seen that this invention is well adapted to attain all of the ends and objectives hereinabove set forth, together with other advantages which are inherent to the apparatus.

It will be understood that certain features and subcombinations are of utility and may be employed without reference to other features and subcombinations. This is contemplated by and is within the scope of the claims.

As many possible embodiments may be made of the invention without departing from the scope thereof, it is to be understood that all matter herein set forth or shown in the figures of the accompanying drawings is to be interpreted as illustrative and not in a limiting sense.

What is claimed is:

1. A strap for preventing the airway obstruction of a user, comprising in combination:
    a support for the chin of the user;
    a first support for a first mandible of the user;
    a second support for the second mandible of the user; and
    means for securing the strap to the head of the user,
        wherein the first mandible support is affixed to one side of the chin support and the second mandible support is affixed to the opposite side of the chin support, wherein when the strap is opened flat, the first mandible support is at an angle to the second mandible support of from about 90 degrees to about 140 degrees.

2. A strap according to claim 1, wherein the first mandible support and the second mandible support are each from about 1.75 inches wide to about 2.25 inches wide.

3. A strap according to claim 1 for a user, wherein when the strap is opened flat, the first mandible support is at an angle to the second mandible support of from about 100 degrees to about 120 degrees.

4. A strap according to claim 1 for a user, wherein when the strap is opened flat, the first mandible support is at an angle to the second mandible support of approximately 110 degrees.

5. A strap according to claim 1 for a user, wherein when the strap is closed, the chin support is at an angle to the main plane of the strap of from about 40 degrees to about 80 degrees.

6. A strap according to claim 1 for a user, wherein when the strap is closed, the chin support is at an angle to the main plane of the strap of from about 50 degrees to about 70 degrees.

7. A strap according to claim 1 for a user, wherein when the strap is closed, the chin support is at an angle to the main plane of the strap of approximately 60 degrees.

8. A strap according to claim 1, wherein the first mandible support and the second mandible support are each from about 1.5 inches wide to about 3 inches wide.

9. A strap according to claim 2 for a user, wherein when the strap is closed, the chin support is at an angle to the main plane of the strap of approximately 60 degrees.

10. A strap according to claim 8 for a user, wherein when the strap is opened flat, the first mandible support is at an angle to the second mandible support of from about 100 degrees to about 120 degrees.

11. A strap according to claim 8 for a user, wherein when the strap is opened flat, the first mandible support is at an angle to the second mandible support of approximately 110 degrees.

12. A strap according to claim 8 for a user, wherein when the strap is closed, the chin support is at an angle to the main plane of the strap of from about 40 degrees to about 80 degrees.

13. A strap according to claim 8 for a user, wherein when the strap is closed, the chin support is at an angle to the main plane of the strap of from about 50 degrees to about 70 degrees.

14. A strap according to claim 8 for a user, wherein when the strap is closed, the chin support is at an angle to the main plane of the strap of approximately 60 degrees.

15. A strap according to claim 2 for a user, wherein when the strap is closed, the chin support is at an angle to the main plane of the strap of from about 40 degrees to about 80 degrees.

16. A strap according to claim 2 for a user, wherein when the strap is closed, the chin support is at an angle to the main plane of the strap of from about 50 degrees to about 70 degrees.

17. A strap according to claim 2 for a user, wherein when the strap is opened flat, the first mandible support is at an angle to the second mandible support of from about 100 degrees to about 120 degrees.

18. A strap according to claim 2 for a user, wherein when the strap is opened flat, the first mandible support is at an angle to the second mandible support of approximately 110 degrees.

* * * * *